US011216074B2

(12) United States Patent
Banerjee et al.

(10) Patent No.: US 11,216,074 B2
(45) Date of Patent: Jan. 4, 2022

(54) MOTION CLASSIFICATION USER LIBRARY

(71) Applicants: Suman Banerjee, Madison, WI (US); Bozhao Qi, Madison, WI (US)

(72) Inventors: Suman Banerjee, Madison, WI (US); Bozhao Qi, Madison, WI (US)

(73) Assignee: OnTracMD, LLC, Sunrise, FL (US)

(*) Notice: Subject to any disclaimer, the term of this patent is extended or adjusted under 35 U.S.C. 154(b) by 0 days.

(21) Appl. No.: 16/818,063

(22) Filed: Mar. 13, 2020

(65) Prior Publication Data

US 2021/0286435 A1 Sep. 16, 2021

(51) Int. Cl.
*G06F 3/01* (2006.01)
*G01P 15/14* (2013.01)

(52) U.S. Cl.
CPC .............. *G06F 3/017* (2013.01); *G01P 15/14* (2013.01); *G06F 3/011* (2013.01)

(58) Field of Classification Search
CPC .......... G01P 15/14; G01P 15/18; G06F 3/014; G06F 3/017; G06F 3/0346; A61B 5/103; A63B 24/0006; A63B 2024/0012
See application file for complete search history.

(56) References Cited

U.S. PATENT DOCUMENTS

| 4,375,674 A | * | 3/1983 | Thornton | ............... | A61B 5/103 273/DIG. 6 |
| 6,007,459 A | * | 12/1999 | Burgess | ................. | G16H 20/30 482/4 |
| 2005/0033200 A1 | | 2/2005 | Soehren et al. | | |
| 2005/0212749 A1 | * | 9/2005 | Marvit | .................. | G06F 3/0346 345/156 |
| 2015/0032034 A1 | * | 1/2015 | Petrigliano | .......... | A61B 5/4585 600/595 |
| 2015/0201867 A1 | | 7/2015 | Peindl et al. | | |
| 2015/0317801 A1 | * | 11/2015 | Bentley | ................ | G08B 21/043 382/107 |
| 2016/0074272 A1 | | 3/2016 | Ahn et al. | | |
| 2016/0084869 A1 | | 3/2016 | Yuen et al. | | |
| 2017/0156657 A1 | | 6/2017 | Flax et al. | | |
| 2018/0000461 A1 | | 1/2018 | Venkataramani | | |

(Continued)

OTHER PUBLICATIONS

Marjorie Skubic, Bradford H Harris, Erik Stone, KC Ho, Bo-Yu Su, and Marilyn Rantz. Testing non-wearable fall detection methods in the homes of older adults. In Engineering in Medicine and Biology Society (EMBC), 2016 IEEE 38th Annual International Conference of the, pp. 557-560. IEEE, 2016.

(Continued)

*Primary Examiner* — Mong-Shune Chung

(57) ABSTRACT

A method includes collecting reference motion data in a device from a motion sensor worn by a user for a movement having a predetermined classification. The motion sensor is attached to a limb having a joint. A user library entry is generated in the device based on the reference motion data and the predetermined classification. Additional motion data is collected in the device from the motion sensor. User motions in the additional motion data corresponding to the user library entry are classified in the device. Range of motion data associated with the user motions is generated in the device. A report is generated in the device including the user motions and the associated range of motion data.

10 Claims, 10 Drawing Sheets

(56) References Cited

U.S. PATENT DOCUMENTS

2018/0153444 A1   6/2018   Yang et al.
2019/0117128 A1*  4/2019   Chen .................. A61B 5/1121

OTHER PUBLICATIONS

P. Lorenzi, R. Rao, A. Suppa, A. Kita, R. Parisi, G. Romano, A. Berardelli, and F. Irrera. Wearable wireless inertial sensors for long-time monitoring of specific motor symptoms in Parkinson's disease, pp. 168-173. SciTePress, 2015.

Sheng Shen, He Wang, and Romit Roy Choudhury. I am a smartwatch and i can track my users arm. In Proceedings of the 14th annual international conference on Mobile systems, applications, and services, 2016.

He Wang, Souvik Sen, Ahmed Elgohary, Moustafa Farid, Moustafa Youssef, and Romit Roy Choudhury. No need to war-drive: unsupervised indoor localization. In Proceedings of the 10th international conference on Mobile systems, applications, and services, pp. 197-210. ACM, 2012.

Pengfei Zhou, Mo Li, and Guobin Shen. Use it free: instantly knowing your phone attitude. In Proceedings of the 20th annual international conference on Mobile computing and networking, pp. 605-616. ACM, 2014.

Guobin Shen, Zhuo Chen, Peichao Zhang, Thomas Moscibroda, and Yongguang Zhang. Walkie-markie: indoor pathway mapping made easy. In Proceedings of the 10th USENIX conference on Networked Systems Design and Implementation, pp. 85-98. USENIX Association, 2013.

Pengfei Zhou, Yuanqing Zheng, Zhenjiang Li, Mo Li, and Guobin Shen. Iodetector: a generic service for indoor outdoor detection. In Proceedings of the 10th ACM Conference on Embedded Network Sensor Systems, pp. 113-126. ACM, 2012.

Peng Liu, Dale Willis, and Suman Banerjee. Paradrop: Enabling lightweight multitenancy at the network's extreme edge. In Edge Computing (SEC), IEEE/ACM Symposium on, pp. 1-13. IEEE, 2016.

Yujie Dong, Adam Hoover, Jenna Scisco, and Eric Muth. A new method for measuring meal intake in humans via automated wrist motion tracking. Applied psychophysiology and biofeedback, 37(3):205-215, 2012.

Donna C Boone and Stanley P Azen. Normal range of motion of joints in male subjects. J Bone Joint Surg Am, 61(5):756-759, 1979.

Brenda L Greene and Steven L Wolf. Upper extremity joint movement: comparison of two measurement devices. Arch Phys Med Rehabil, 70(4):288-90, 1989.

JM Walker, Debbie Sue, Nancy Miles-Elkousy, Gail Ford, and Helen Trevelyan. Active mobility of the extremities in older subjects. Physical therapy, 64(6):919-923, 1984.

Abhinav Parate, Meng-Chieh Chiu, Chaniel Chadowitz, Deepak Ganesan, and Evangelos Kalogerakis. Risq: Recognizing smoking gestures with inertial sensors on a wristband. In Proceedings of the 12th annual international conference on Mobile systems, applications, and services, pp. 149-161. ACM, 2014.

Stanley H Chan, Ramsin Khoshabeh, Kristofor B Gibson, Philip E Gill, and Truong Q Nguyen. An augmented agrangian method for total variation video restoration. Image Processing, IEEE Transactions on, 20(11):3097-3111, 2011.

Meinard Muller. Dynamic time warping. Information retrieval for music and motion, pp. 69-84, 2007.

Stan Salvador and Philip Chan. Toward accurate dynamic time warping in linear time and space. Intelligent Data Analysis, pp. 561-580, 2007.

Chao Xu, Parth H Pathak, and Prasant Mohapatra. Finger-writing with smartwatch: A case for finger and hand gesture recognition using smartwatch. In Proceedings of the 16th International Workshop on Mobile Computing Systems and Applications, pp. 9-14. ACM, 2015.

Shahriar Nirjon, Jeremy Gummeson, Dan Gelb, and Kyu-Han Kim. Typingring: A wearable ring platform for text input. In Proceedings of the 13th Annual International Conference on Mobile Systems, Applications, and Services, pp. 227-239. ACM, 2015.

He Wang, Ted Tsung-Te Lai, and Romit Roy Choudhury. Mole: Motion leaks through smartwatch sensors. In Proceedings of the 21st Annual International Conference on Mobile Computing and Networking, pp. 155-166. ACM, 2015.

Xiangyu Liu, Zhe Zhou, Wenrui Diao, Zhou Li, and Kehuan Zhang. When good becomes evil: Keystroke inference with smartwatch. In Proceedings of the 22nd ACM SIGSAC Conference on Computer and Communications Security, pp. 1273-1285. ACM, 2015.

Harishchandra Dubey, Jon C Goldberg, Mohammadreza Abtahi, Leslie Mahler, and Kunal Mankodiya. Echowear: smartwatch technology for voice and speech treatments of patients with parkinson's disease. In Proceedings of the conference on Wireless Health, p. 15. ACM, 2015.

* cited by examiner

MOTION CLASSIFICATION USER LIBRARY

BACKGROUND

Field of the Disclosure

The present disclosure relates generally to classifying motions using a motion sensor and libraries, such as general libraries and user libraries.

Description of the Related Art

Aging, trauma, and osteoarthritis are the leading causes of joint pain and dysfunction. Beginning around the age of 30, human joint functions become more restricted. This restriction is due to muscle loss, changes in cartilage, and variations in connective tissue. These changes tend to increase stress on certain joints and make the joints less resilient and more susceptible to damage. One technique to assess joint function is to measure its full movement potential, also known as a range of motion (ROM). Traditionally, health care providers evaluate range of motion with a universal goniometer or an inclinometer. A key factor in goniometric measurement is to accurately align the goniometer against the subject's body, i.e., aligning the center fulcrum of the goniometer over the right body joint and making sure the two arms are parallel to the corresponding body parts.

Despite being the most widely used tools in clinical practice, traditional measurement tools like the goniometer and inclinometer present some key challenges. Since they require taking a manual readout of the angle, they are susceptible to variances in inter-rater reliability and can lead to different results. Another disadvantage is that the starting position, the center of rotation, and the true vertical and horizontal positions can only be visually estimated. Moreover, the universal goniometer must be held with two hands, which leaves neither hand free for stabilization of the subject's body or joint.

BRIEF DESCRIPTION OF THE DRAWINGS

The present disclosure may be better understood, and its numerous features and advantages made apparent to those skilled in the art, by referencing the accompanying drawings. The use of the same reference symbols in different drawings indicates similar or identical items.

DETAILED DESCRIPTION

Figure 1:
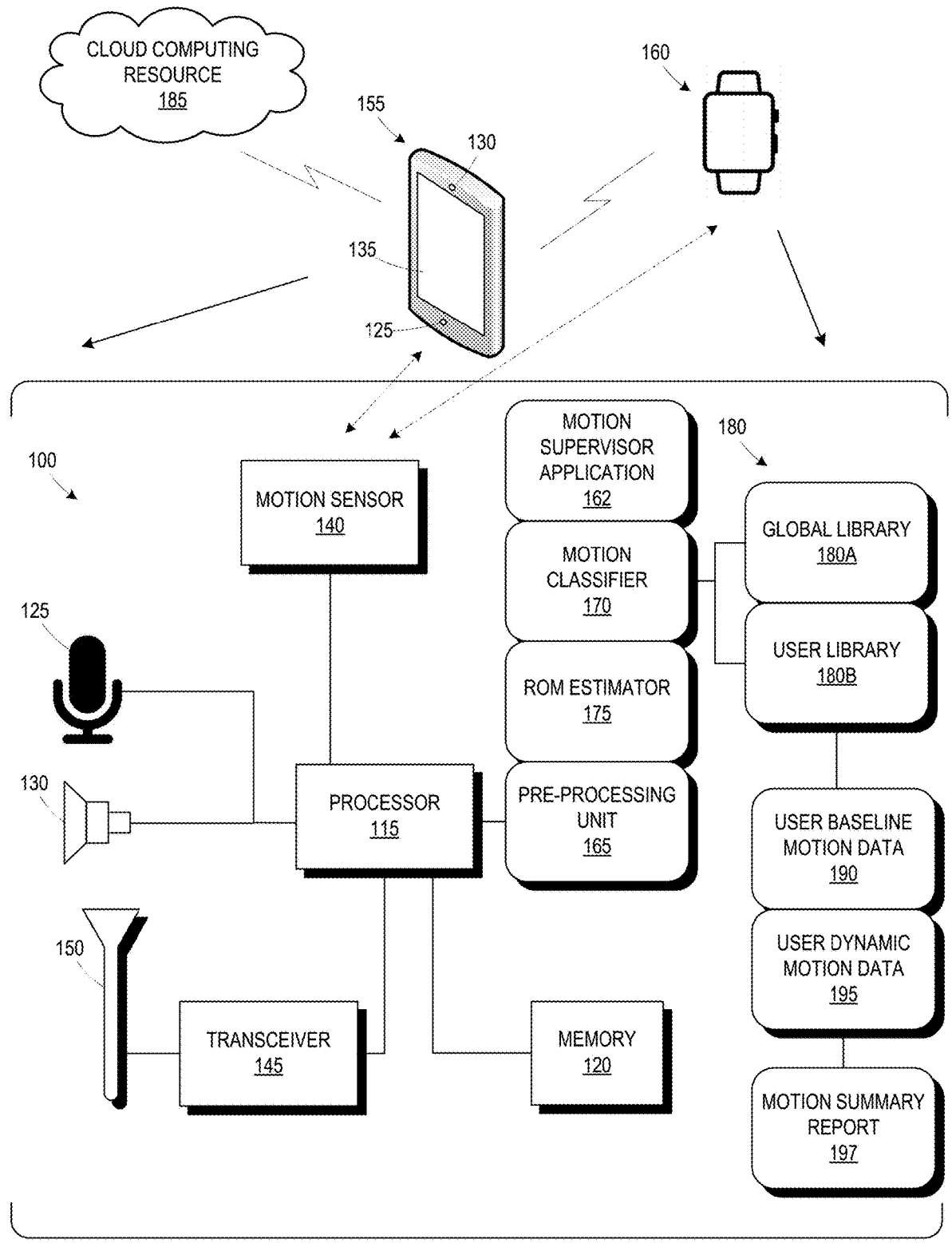
FIG. 1 is a simplified block diagram of a joint motion system in accordance with some embodiments.

FIGS. 1-12 illustrate example techniques for determining joint motion. FIG. 1 is a simplistic block diagram of a motion sensing system 100. The system may include, among other things, a processor 115, a memory 120, a microphone 125, a speaker 130, a display 135, and a motion sensor 140 (e.g., an accelerometer, magnetometer, mercury switch, gyroscope, compass, or some combination thereof). The memory 120 may be a volatile memory (e.g., DRAM, SRAM) or a non-volatile memory (e.g., ROM, flash memory, hard disk, etc.). In some embodiments, the system 100 includes a transceiver 145 for transmitting and receiving signals via an antenna 150. The transceiver 145 may include one or more radios for communicating according to different radio access technologies, such as cellular, Wi-Fi, BLU-ETOOTH®, Zigbee, etc.

In some embodiments, portions of the system 100 are implemented on different devices. For example, the processor 115, memory 120, and transceiver 145 may be implemented on a mobile device 155, such as a smartphone, and the motion sensor 140 nay be implemented on a motion sensing device 160 remote from the mobile device 155, such as a smartwatch or dedicated motion sensor. The mobile device 155 may communicate with the motion sensing device 160 using the transceiver 145.

In some embodiments, the system 100 may be implemented on a single device, such as on a smartwatch implementing the processor 115, the memory 120, the transceiver 145, and the motion sensor 140.

In the system 100, the processor 115 may execute instructions stored in the memory 120 and store information in the memory 120, such as the results of the executed instructions. Some embodiments of the processor 115 and the memory 120 may be configured to implement motion supervisor application 162, a pre-processing unit 165, a motion classifier 170, and a range of motion (ROM) estimator 175. The motion classifier 170 employs a gesture library 180. In some embodiments, the gesture library 180 includes a global library 180A, and a user library 180B. The global library 180A includes library entries for a variety of reference motions. The user library 180B includes entries specific to a user of the system 100. The transceiver 145 may also communicate over a packet-based communication network, such as the Internet. In one embodiment, a remote computing resource 185 may interface with the device 100 to implement one or more of the functions described herein. In some embodiments, the motion supervisor application 162 directs the operation of the various other units 165, 170, 175 for collecting motion classification and range of motion data.

Range of joint motion is used to evaluate the impairment level of joint function or assess the rehabilitation status. There are two types of ROM: passive range of motion (PROM) and active range of motion (AROM). PROM is the arc of motion attained by an examiner without assistance from the subject, while AROM is the arc of motion attained by a subject during unassisted voluntary joint motion. If a subject can complete active ROM easily and painlessly, further testing of that motion may not be needed. Otherwise, additional testing such as passive ROM should be conducted. Passive motion measurement provides an examiner with information about the integrity of the joint surfaces and the extensibility of the joint capsule and associated tissues. Normally passive ROM is slightly greater than active ROM because the joint has a small amount available motion that is not under voluntary control.

Figure 2:
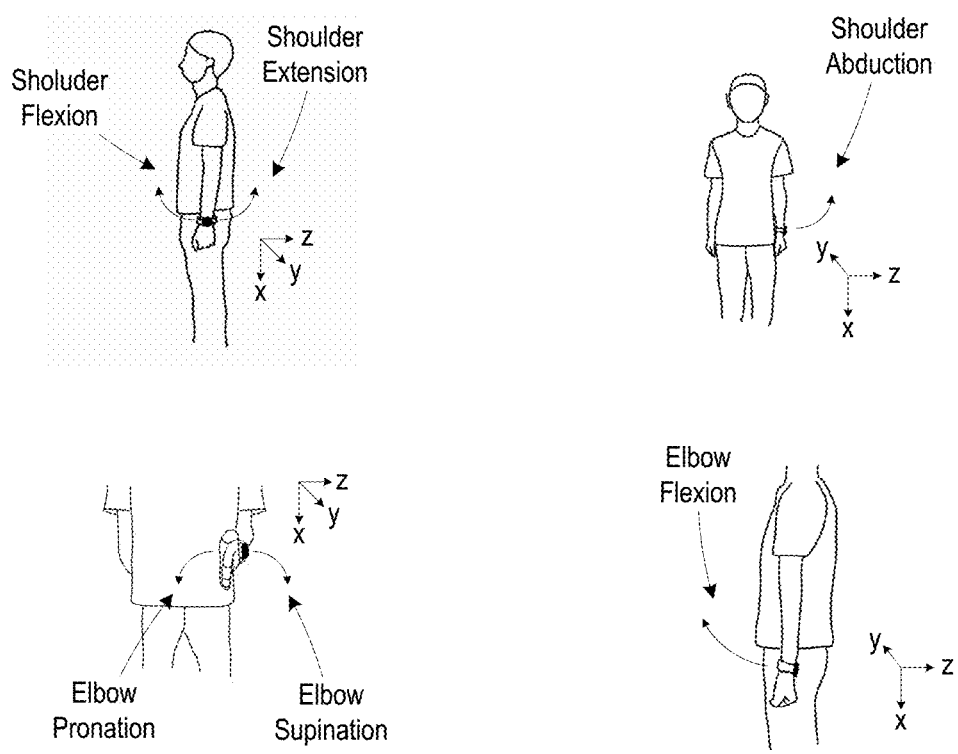
FIG. 2 is a diagram illustrating example joint motions, in accordance with some embodiments.

FIG. 2 is a diagram illustrating example joint motions, which may be evaluated using both AROM and PROM, in accordance with some embodiments. The orientations in FIG. 2 represent initial orientations for the motion sensor 140. Example joint motions include, flexion: the movement in which two body parts with common articulation bend toward each other; extension: the movement in which two body parts with common articulation extend away from each other; abduction: the lateral movements of the body part away from the vertical axis of the torso; pronation: the rotation of the hand and forearm so that the palm faces backwards or downwards; and supination: the rotation of the forearm and hand so that the palm faces forward or upward. Normative ROM values for the motions illustrated in FIG. 2 include shoulder flexion −180°, shoulder extension −60°, shoulder abduction −180°, elbow pronation −80°, elbow supination −80°, and elbow flexion −150°. Range of joint motion differs slightly among people.

The example joint motions illustrated in FIG. 2 are not limiting, as the techniques described herein may be applied to other joint motions. The evaluation of arm motions is also not limiting. Other joint motions may be monitored, such as leg joint motions, by mounting the motion sensor to a subject's leg. An example list of joint motions include, but are not limited to, shoulder flexion, shoulder extension, shoulder abduction, elbow supination, elbow pronation, elbow flexion, elbow extension, vertical internal rotation, vertical external rotation, horizontal internal rotation, horizontal external rotation, knee extension, knee flexion, hip abduction, and hip adduction.

Figure 3:
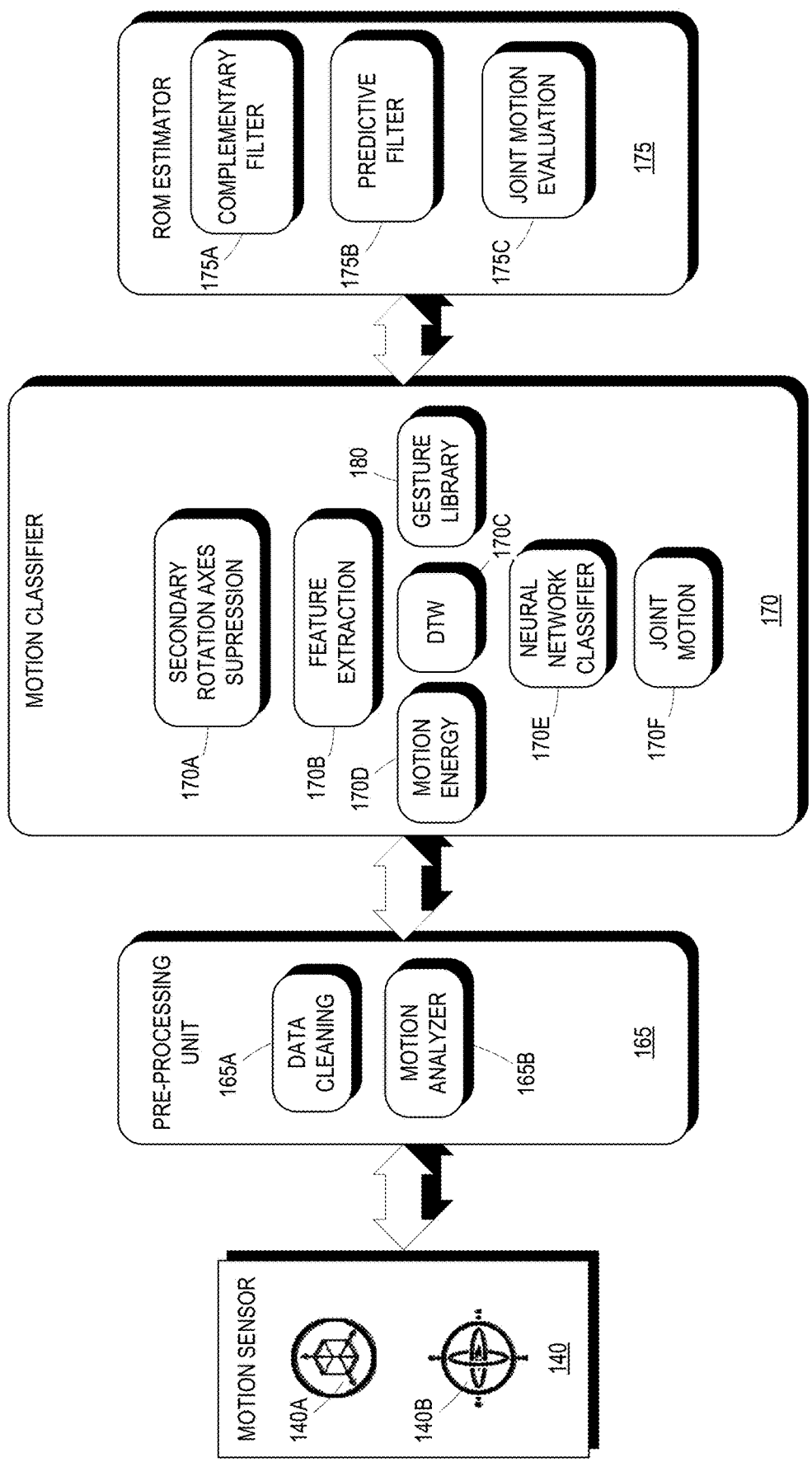
FIG. 3 is a simplified block diagram illustrating the interface between and operation of elements of the system of FIG. 1, in accordance with some embodiments.

FIG. 3 is a simplified block diagram illustrating the interface between and operation of the motion sensor 140, the pre-processing unit 165, the motion classifier 170, and the ROM estimator 175 of FIG. 1, in accordance with some embodiments. The motion sensor 140 includes a 3-axis accelerometer 140A and a 3-axis gyroscope 140B. The sensor data from the motion sensor 140 is received by the pre-processing unit 165. The pre-processing unit 165 reduces noise contained in raw sensor data, extracts a corresponding motion interval, and determines a primary axis of rotation for the motion. The set of data readings from the motion sensor 140 during the identified motion interval defines a motion interval data set that is further analyzed. The motion interval data set is sent to the motion classifier 170. In some embodiments, the motion classifier 170 compares the motion interval data set with samples in the gesture library 180 using a dynamic time warping technique to attempt to classify the associated motion. In some embodiments, the motion classifier 170 uses a neural network for classifying the motion. The ROM estimator 175 calculates the range of motion for the associated motion using the motion interval data.

Figure 4:
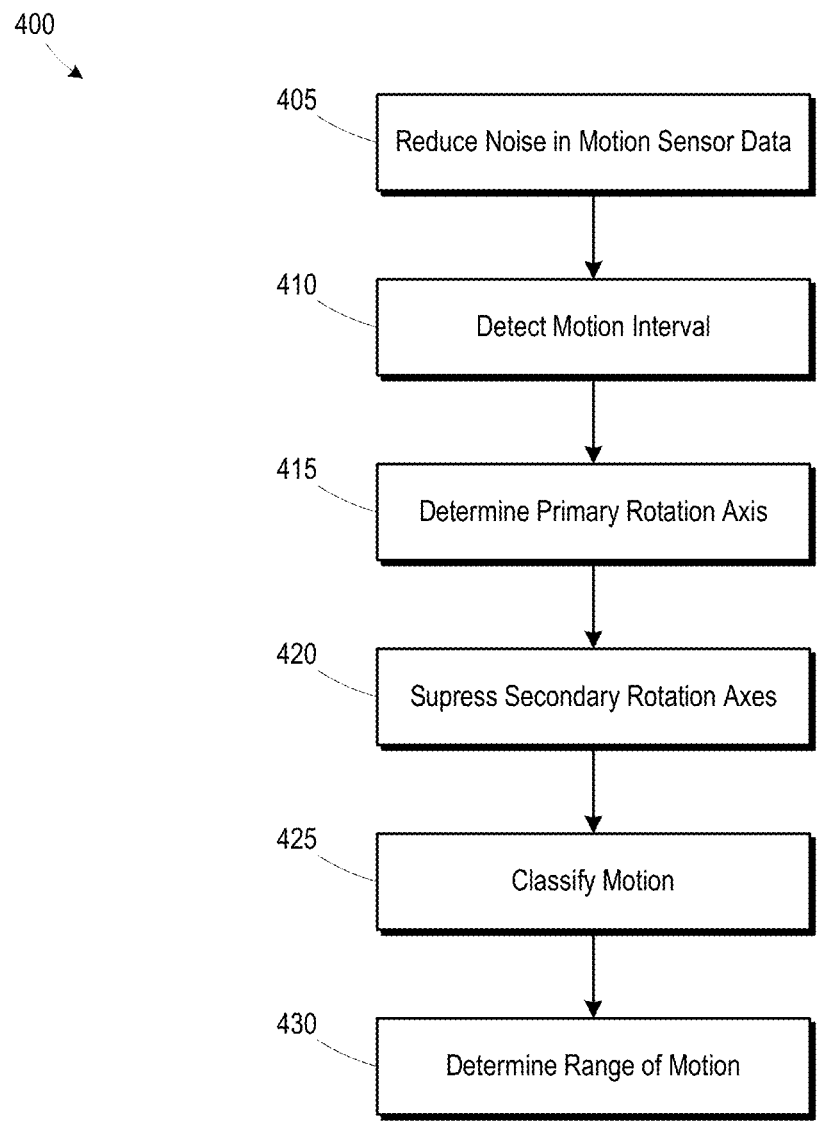
FIG. 4 is a flow diagram of an illustrative method for identifying a motion, classifying the motion, and determining a range of movement measurement for the motion using motion sensor data, in accordance with some embodiments.

FIG. 4 is a flow diagram of an illustrative method 400 for identifying a motion, classifying the motion, and determining a range of movement measurement for the motion using motion sensor data, in accordance with some embodiments disclosed herein. In some embodiments, various elements of the method 400 shown in FIG. 4 are implemented by the system 100. In some embodiments, the remote computing resource 185 (see FIG. 1) may also be used to perform one or more elements of the method 400. The operation of the pre-processing unit 165, the range of motion (ROM) estimator motion classifier 170, and the range of motion (ROM) estimator 175 are also described in reference to FIG. 4.

Figure 5:
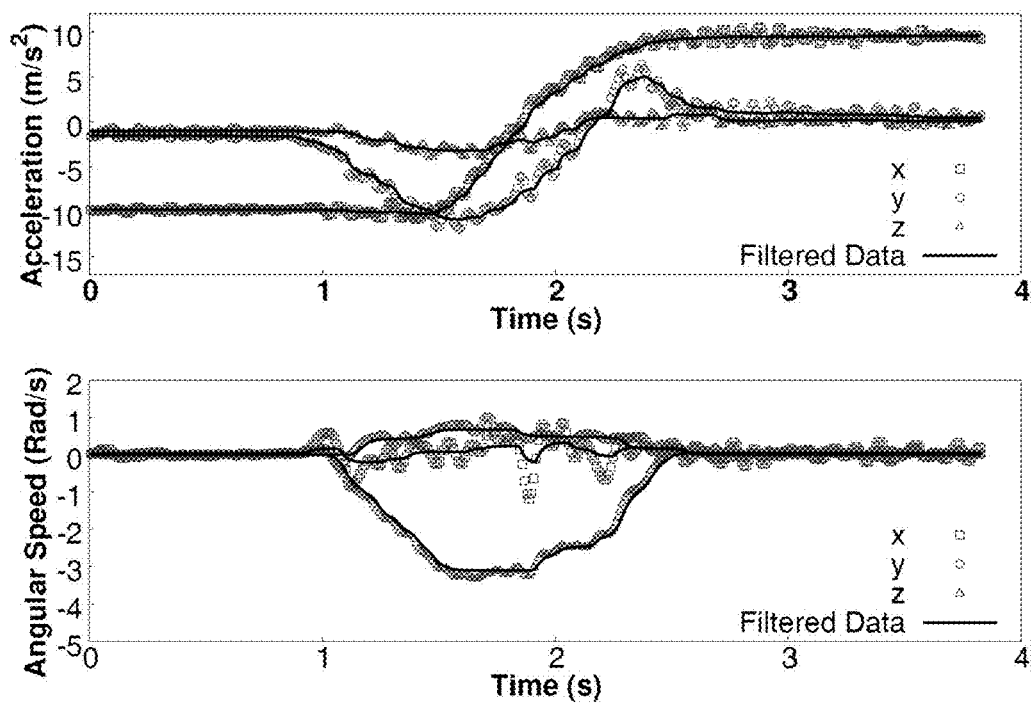
FIG. 5 is a diagram illustrating raw data and the resulting denoised data, in accordance with some embodiments.

In addition to hardware generated noise, the motion sensor 140 is sensitive to tiny, shaky, and vibrating movements, which may add extra noise to measurement data. To increase measurement accuracy, the pre-processing unit 165 reduces noise in the motion sensor data in method block 405 (see FIG. 4). The pre-processing unit 165 includes a data cleaning module 165A for reducing noise in the data received from the motion sensor 140. The orientation of the motion sensor 140 may change dramatically, resulting in a sharp transition. The data cleaning module 165A reduces noise while maintaining the sharp transitions in the raw data. In some embodiments, the data cleaning module 165A uses a total variation denoising (TVD) technique. The TVD procedure minimize the objective function:

$$\min obj = \mu k x - y k^2 + \rho k D x k_1 \qquad (1)$$

where x is the denoised signal, y is the raw signal, and D is a finite differential operator. The parameters µ and ρ are adjusted according to the noise level and signal characteristics. FIG. 5 is a diagram illustrating raw data and the resulting denoised data, in accordance with some embodiments. Note that the small variations in the raw data are removed while the sharp transitions are maintained.

Figure 6:
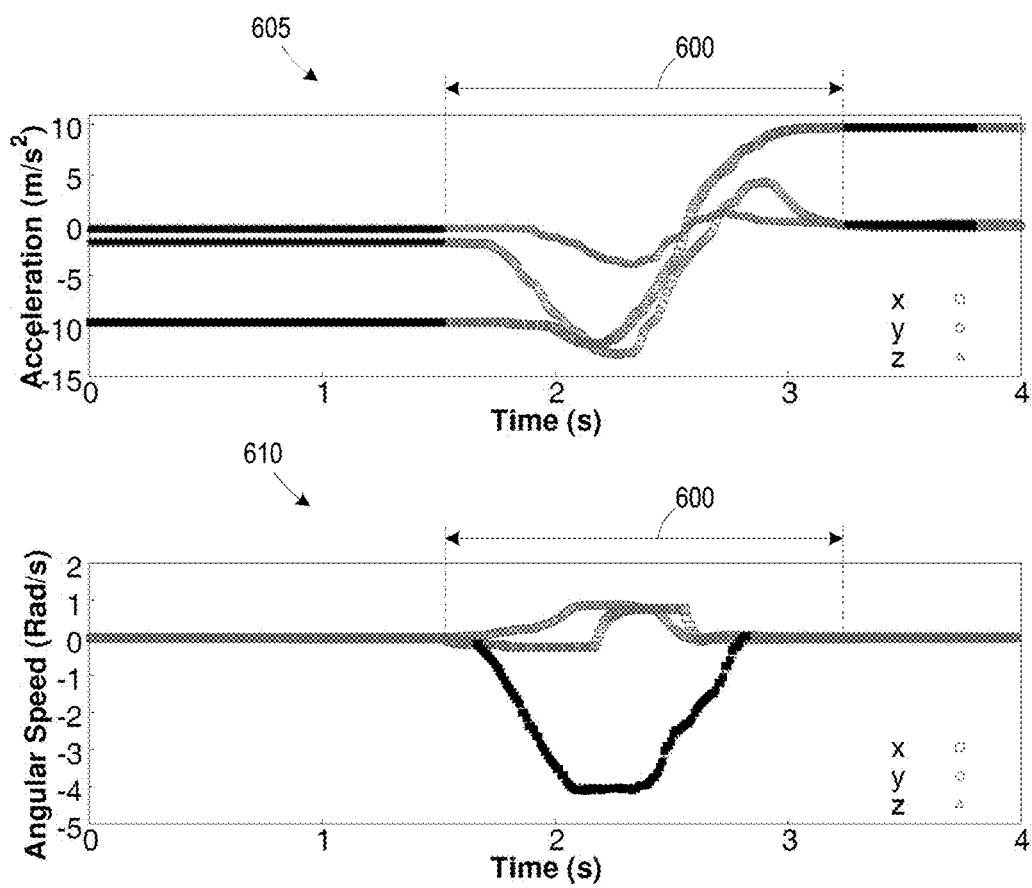
FIG. 6 is a diagram illustrating motion data for an example shoulder flexion motion, in accordance with some embodiments.

The pre-processing unit 165 includes a motion analyzer 165B that identifies motion intervals for analysis and identifies the primary rotation axis. In method block 410, the motion analyzer 165B detects a motion interval. In some embodiments, the motion analyzer 165B uses a pattern recognition technique to extract a motion interval. FIG. 6 is a diagram illustrating motion data for an example shoulder flexion motion, in accordance with some embodiments. In some embodiments, the motion analyzer 165B employs an extraction technique based on the principle of dispersion to identify a motion interval 600. The dispersion technique includes three input variables, a sliding window size, a trigger threshold ($T_{th}$), and an influence factor (IF). A sliding window size of 10 corresponds to the last 10 readings. The motion analyzer 165B calculates the mean and standard deviation for the sliding window. The trigger threshold value relates to the relationship between the standard deviation and the mean calculated for the sliding window. In some embodiments, a motion interval 600 is started responsive to the current sample exceeding the mean of the sliding window by a trigger factor computed by multiplying the standard deviation of the sliding window by the trigger threshold:

$$\text{TriggerEvent} = x > \bar{x} + T_{th} * \sigma. \qquad (2)$$

For example, for a trigger threshold of $T_{th}=2$, a trigger event is identified responsive to a new reading being two standard deviations away from the sliding window mean. The current factor, x is added to the sliding window using the influence factor:

$$\hat{x}_i = IF * x_i + (1-IF) * x_{i-1}. \tag{3}$$

The influence factor describes the importance of the new reading relative to the previous readings and is used to smooth the incoming reading.

The motion interval 600 is terminated when the difference between the current sample and the sliding window drops back below the trigger factor. In some embodiments, the motion analyzer 165B may terminate only after a predetermined number of samples (e.g., 1-4) are received having a difference from the mean less than the trigger factor. In some embodiments, separate motion intervals are detected separately for each gyroscope axis.

In method block 415, the motion analyzer 165B determines a primary rotation axis for the motion included in the motion interval 600. The motion sensor 140 detects movements in x, y and z-axis regardless of the orientation of the motion sensor 140. For each joint motion, the motion sensor 140 is actually rotating around a single axis, and the ROM value can be calculated by integrating the gyroscope values of that axis. Referring to FIG. 6, the curve 605 represents data for a shoulder flexion ROM when the arm wearing the motion sensor 140 is rotating only around the z-axis. During this motion, the readings of the accelerometer 140A along the z-axis stay somewhat stable compared to those of the other two axes.

For some joint motions, e.g., shoulder abduction and flexion, the subject may rotate along elbow joints during the major movement process. The curve 610 represents data for a shoulder flexion ROM when the arm wearing the motion sensor 140 exhibits minor rotation movements during the motion. Although the major rotation axis for shoulder flexion is still the z-axis, there are movements along all three axes.

The motion analyzer 165B uses both the accelerometer and the gyroscope data to find the primary rotation axis for a given motion interval 600. First, the motion analyzer 165B finds $axis_{std}$, the axis with the minimum standard deviation of acceleration values. Next, the motion analyzer 165B finds $axis_{gyro}$ the axis with the maximum rotation angle using the gyroscope values. If $axis_{std}$ and $axis_{gyro}$ match, the corresponding axis is selected as the rotation axis. If $axis_{std}$ and $axis_{gyro}$ do not match, it indicates that minor rotation happened during the motion. The motion analyzer 165B checks which axis senses the gravity in the initial phase of the motion. The axis which senses gravity cannot be the rotation axis and is eliminated from the candidate list. Any minor rotation that is present generally happens during an intermediate portion of the motion. The gyroscope sensor 140B senses this minor movement after the major motion starts. Hence, based on the gyroscope readings, the motion analyzer 165B determines which axis started to rotate first and labels it as $axis_{first}$. The motion analyzer 165B uses a majority voting technique from the candidates including $axis_{std}$, $axis_{gyro}$, and $axis_{first}$ to designate the primary rotation axis.

In method block 420, the secondary rotation axes are suppressed. In some embodiments, the secondary axes are suppressed both for motion classification and range of motion determination. Techniques for suppressing the secondary rotation axes are described in greater detail below for the motion classifier 170 and the ROM estimator 175.

In method block 425 the motion classifier 170 receives the motion interval data from the pre-processing unit 165 and classifies the associated motion. The motion data stream from the pre-processing unit 165 includes a 3-axis accelerometer vector and a 3-axis gyroscope vector. In some embodiments, the accelerometer and gyroscope vectors are time synchronized and merged to define a 6-axis stream. The motion analyzer 165B determined the primary rotation axis, as described above. For purposes of this illustration, the two axes other than the primary rotation axis are referred to as secondary rotation axes. The motion classifier 170 includes a secondary rotation axes suppression module 170A. In some embodiments, the secondary rotation axes suppression module 170A isolates the primary rotation movement by setting the gyroscope values for the secondary rotation axes in the gyroscope vector to zero and setting the accelerometer values for the primary rotation axis to zero. The modified sensor stream thus isolates the motion data associated with the primary rotation axis.

In some embodiments, the motion classifier 170 includes a feature extraction module 170B that uses a reduction technique to extract features from the motion data. In some embodiments, the feature extraction module 170B uses a Principal Component Analysis (PCA) technique to reduce the number of variables and extract core features from the collected dataset. PCA eliminates the least important features in the dataset and provides simplicity and interpretability of variables. PCA combines input variables in a specific manner that retains the most valuable features of all of the variables. The feature extraction module 170B applies PCA the accelerometer and gyroscope dataset to extract core features from them. PCA also serves to increase the speed of the data analysis process. The feature extraction module 170B normalizes the data:

$$X^* = \frac{X - \mu}{\delta}, \tag{4}$$

where μ and σ are the mean and the standard deviation of the sample data.

The feature extraction module 170B calculates the covariance matrix:

$$\text{Matrix(Covariance)} = \begin{bmatrix} Var[X_1] & Cov[X_1, X_2] \\ Cov[X_2, X_1] & Var[X_2] \end{bmatrix}, \tag{5}$$

where $X_1$ is the accelerometer reading vector, $X_2$ is the gyroscope reading vector, and.

$$Var[X_1] = Cov[X_1, X_1] \text{ and } Var[X_2] = Cov[X_2, X_2]. \tag{6}$$

The Eigen decomposition is performed on the covariance matrix Matrix(Covariance), which is a d×d matrix, where each element represents the covariance between two features. The covariance between two features is calculated as:

$$Cov[X_j, X_k] = \frac{1}{n-1} \sum_{i=1}^{n} (x_{ij} - \bar{x}_j)(x_{ik} - \bar{x}_k). \tag{7}$$

The calculation of the covariance matrix is summarized by:

$$\text{Matrix(Covariance)} = \frac{1}{n-1}((X - x)^T (X - \bar{x})), \tag{8}$$

where $\bar{x}$ is the mean vector:

$$\bar{X} = \frac{1}{n}\sum_{i=1}^{n} x_i. \quad (9)$$

The mean vector is a d—dimensional vector where each value in the vector represents the sample mean of a feature column in the dataset.

The eigenvalues and eigenvectors are calculated for the covariance matrix. Since the covariance matrix is a square matrix, $\lambda$ is an eigenvalue for a matrix A if it is a solution of the characteristic equation:

$$\det(\lambda I - A) = 0, \quad (10)$$

where, I is the identity matrix of the same dimension as A which is a required condition for the matrix subtraction as well in this case and 'det' is the determinant of the matrix. For each eigenvalue $\lambda$, a corresponding eigenvector v, can be found by solving:

$$(\lambda I - A)v = 0. \quad (11)$$

The eigenvalues are ordered from largest to smallest to provide the components in order of significance. The eigenvector corresponding to the highest eigenvalue is the principal component of the dataset. Since the accelerometer and gyroscope dataset has two variables, there are two corresponding eigenvalues and eigenvectors. A feature vector is formed using a matrix of the eigenvectors:

$$\text{Feature Vector} = (V_1, V_1). \quad (12)$$

Since the eigenvectors indicates the direction of the principal components (new axes), the original data is multiplied by the eigenvector matrix to re-orient the data onto the new axes. This re-oriented data is called a score:

$$Sc = [\text{Orig.data}] \cdot [v]. \quad (13)$$

The feature extraction module 170B generates a score vector for the incoming motion interval data.

The motion classifier 170 includes a dynamic time warping (DTW) module 170C that employs the gesture library 180 to classify the motion associated with the motion interval data. Each entry in the gesture library 180 has an associated motion label, or classification. For example, different subsets of the library entries are associated with different motions, such as shoulder flexion, shoulder extension, shoulder abduction, elbow supination, elbow pronation, elbow flexion, elbow extension, vertical internal rotation, vertical external rotation, horizontal internal rotation, horizontal external rotation, knee extension, knee flexion, hip abduction, or hip adduction.

DTW is a dynamic programming technique used to measure similarity between two temporal sequences. DTW is useful in identifying similar motions with varying speeds or with intermediate accelerations and decelerations. The sequences are "warped" non-linearly by shrinking or stretching along the time dimension to determine a measure of their similarity. This warping is useful in gesture recognition, where different users may perform the same motions at different speeds, and the motions may involve stops.

DTW evaluates the similarity between two temporal sequences. Based on the similarity of two sequences, it can be inferred whether the two sequences are measured during the same motion. The DTW module 170C can detect similarities in joint motion patterns even if one person conducts the same joint motion faster than the other, or if there were accelerations and decelerations during the course of an observation. The gesture library 180 stores sample temporal sequences of each joint motion.

Figure 7:
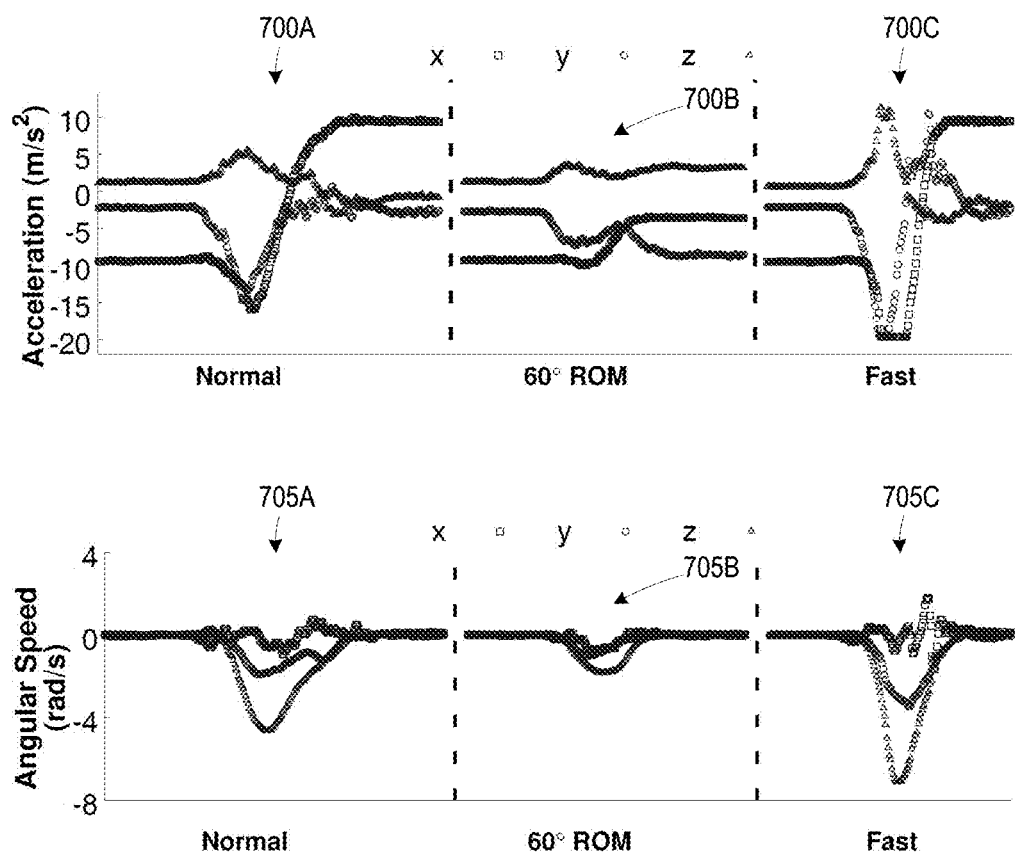
FIG. 7 is a diagram illustrating raw accelerometer and gyroscope values for three variations of shoulder flexion, in accordance with some embodiments.

In general, speed and range of motion are two factors that can change between two motions. FIG. 7 shows raw accelerometer and gyroscope values for three variations of shoulder flexion, in accordance with some embodiments. The curves 700A, 700B show accelerometer and gyroscope data, respectively, for a baseline motion representing 50° shoulder flexion performed at normal speed. The curves 705A, 705B, 700C show accelerometer data, and the curves 705A, 705B, 705C show gyroscope data for a 60° shoulder flexion, which represents a subsequence of the normal motion. Note that the gyroscope curves 700B, 705B have the same shape but different magnitudes due to a shorter rotation. The curves 710A, 710B show accelerometer data when the motion is performed quickly. The shape of the signal, for both the accelerometer and the gyroscope data shrinks along the time axis. The DTW module 170C and gesture library 180 are configured to accommodate such variations. The gesture library 180 includes entries for the typical variations for each motion.

DTW involves matching the incoming temporal sequence to entries in the gesture library 180 that represent predefined motions with known classifications (e.g., motion label as described above in reference to FIG. 2). In some embodiments, the incoming temporal sequence is the score data described in reference to Equation 13 above, which represents PCA features extracted from the accelerometer and gyroscope time sequence data. The score data is a three-dimensional vector that includes a component for each of the x, y, and z axes. The incoming score data for a given motion interval is compared against all motions in the gesture library 180 and a distance measure is generated by the DTW module 170C for each entry in the gesture library 180 representing how closely the incoming temporal sequence matches the associated gesture library entry.

The distance between two sequences can be calculated using:

$$D(i,j) = |A(i) - B(j)| + \min\begin{Bmatrix} D(i-1, j) \\ D(i-i, j-1) \\ D(i, j-1) \end{Bmatrix}, \quad (14)$$

where A and B are the temporal data sequences.

Figure 8:
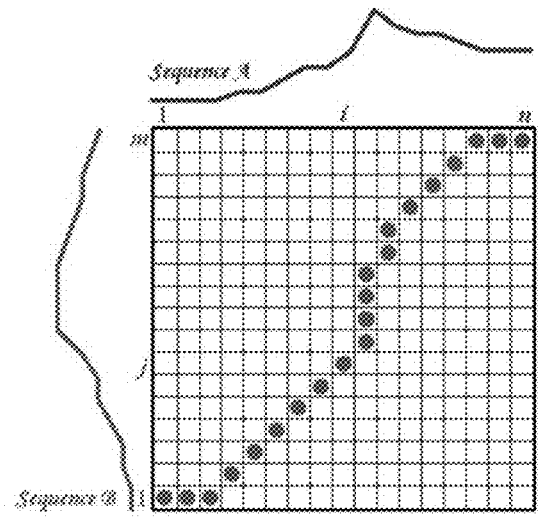
FIG. 8 is a diagram illustrating a technique to determine the minimum distance between the two temporal sequences using dynamic programming, in accordance with some embodiments.

FIG. 8 is a diagram illustrating the application of Equation 14 to determine the minimum distance between the two temporal sequences using dynamic programming, in accordance with some embodiments.

The DTW module 170C employs a k-Nearest Neighbor technique to predict a label for the unseen data. In some embodiments, the matching using the gesture library 180 is performed separately for each axis in the score data, resulting in three sets of candidate distance measures. The matching performed for each of the three axis streams returns k-Nearest Neighbors, where the values of k are dependent on the size of the labeled dataset. The DTW module 170C employs majority voting across all 3*k motion labels to determine the types of motion. Ties are broken by taking the label with the least wrap distance. The distance score associated with selected entry in the gesture library 180 represents a confidence metric associated with the classification.

Physiotherapy settings are usually very controlled and subjects begin any motion with the same initial orientation (e.g., see the initial positions in FIG. 2). However, in some instances the person wearing the motion sensor 140 starts a motion with a different initial orientation of the motion sensor 140. For example, a subject may perform an elbow flexion, but with the initial position as shown in shoulder flexion. This situation represents a change in the yaw angle, which cannot be detected using only accelerometer or gyroscope measurements. If additional entries were added to the gesture library 180 to account for different initial positions, could lead to a misclassification of other motions. For example, the raw signals from shoulder flexion and elbow flexion with the same initial orientation are highly correlated, and the DTW distance metric alone is not sufficient to distinguish such motions. To deal with such conflicting motions, the motion classifier 170 includes a motion energy module 170D, according to some embodiments. Motion energy is computed using data from the accelerometer 140A and the gyroscope 140B. Different motions, such as shoulder motions and elbow motions have different and separable energies. The motion energy module 170D use a prefiltering approach that uses the motion energy to classify the incoming motion as a shoulder or an elbow motion. The motion energy module 170D calculates a penalty term to the distance estimate from the DTW module 170C.

$$\text{Similarity} = DTW_{distance} + \alpha * \sqrt{(g_i - g_j)^2 + (a_i - a_j)^2}, \quad (15)$$

wherein i represents the motion energy of the library entry and j represents the motion energy of the incoming motion based on gyroscope data, g, or acelerometer data, a, and $\alpha$ represents a configurable weighting parameter.

To calculate the motion energy, a Fourier Transform is applied to the accelerometer data and the gyroscope data separately. The Fourier Transform returns a two-sided spectrum in complex form (with real and imaginary parts). A magnitude and a phase can be derived from the complex form. The magnitude of the Fourier Transform is employed to calculate the motion energy using:

$$\text{motion energy} = \\ \sum_{k=0}^{N} \text{magnitute of } FFT(\text{data}_{x-axis})_k * \text{magnitude of } FFT(\text{data}_{x-axis})_k + \\ \sum_{k=0}^{N} \text{magnitute of } FFT(\text{data}_{y-axis})_j * \text{magnitude of } FFT(\text{data}_{y-axis})_k + \\ \sum_{k=0}^{N} \text{magnitute of } FFT(\text{data}_{z-axis})_j * \sum_{k=0}^{N} \text{magnitude of } FFT(\text{data}_{z-axis})_k$$

In some embodiments, the motion classifier 170 includes a design a neural network classifier module 170E that employs a deep neural network (DNN) model to predict the type of joint motion. In general, a DNN model contains three layers: an input layer, a hidden layer, and an output layer. The DNN model receives the incoming temporal sequence defined by the score data described in reference to Equation 13 above, which represents PCA features extracted from the accelerometer and gyroscope time sequence data. The score data is a three-dimensional vector that includes a component for each of the x, y, and z axes. The DNN model is trained using known motion sequences to configure the hidden layer. The motion sequences may include fast and slow motions with different range of motions. The output of the DNN model is a predicted motion type and a probability metric representing the confidence level of the classification.

In some embodiments, the motion classifier 170 includes a joint motion module 170F that compares the motion classifications provided by the DTW module 170C and the neural network classifier 170E. If there is disagreement between the motion classifications, the joint motion module 170F selects the classification having the highest confidence metric.

In method block 430, the ROM estimator 175 determines the ROM for the joint motion associated with the motion interval. The ROM estimator 175 receives the motion interval data from the pre-processing unit 165. In some embodiments, the ROM estimator 175 includes a complementary filter 175A and a predictive filter 175B that generate independent measurements of ROM.

Figure 9:
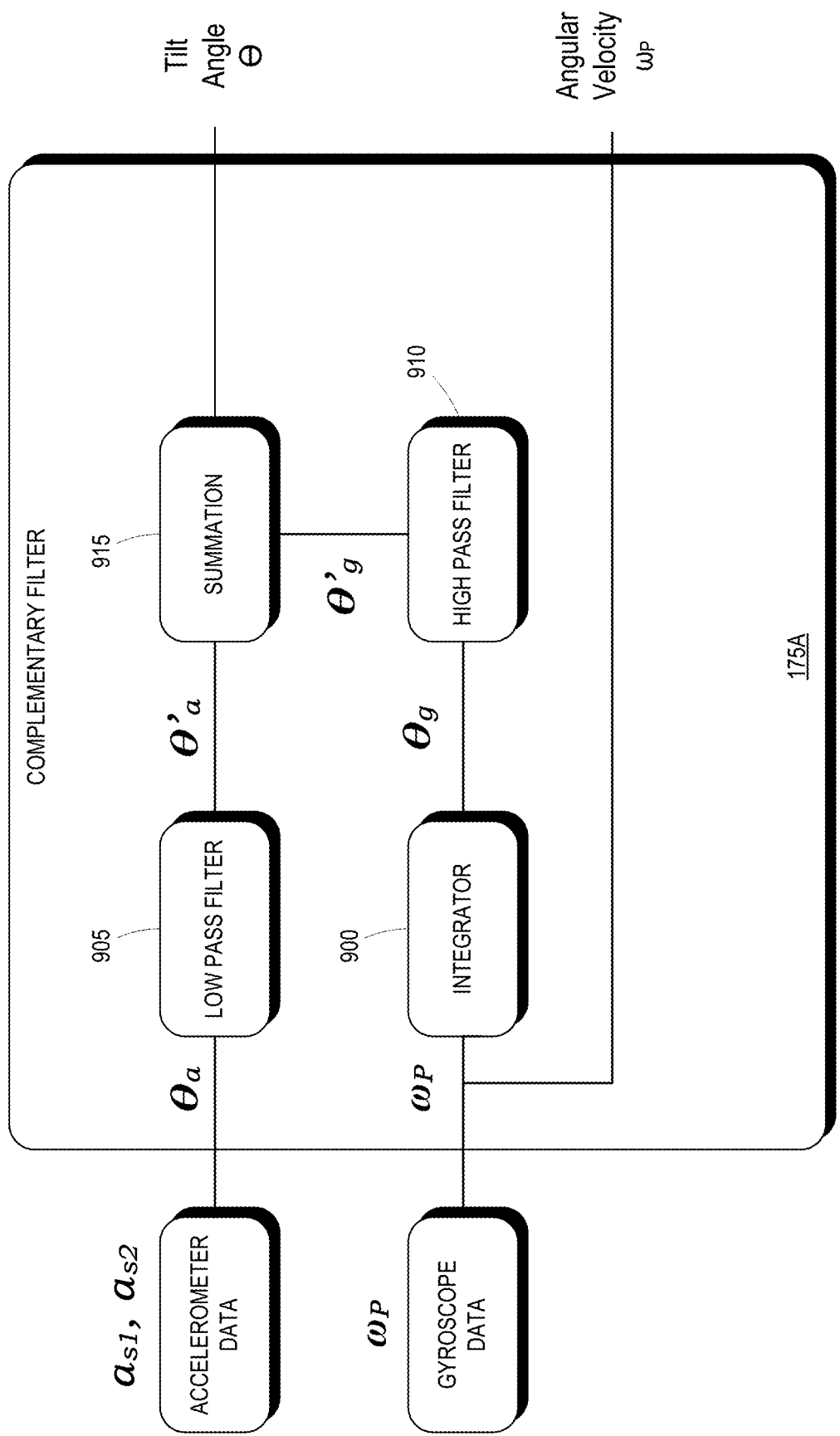
FIG. 9 is a simplified block diagram of a complementary filter, in accordance with some embodiments.

FIG. 9 is a simplified block diagram of the complementary filter 175A, in accordance with some embodiments. The complementary filter 175A fuses data from the accelerometer and the gyroscope. In some embodiments, the input data for the complementary filter 175A includes data for which the suppression of the secondary rotation axes described in method block 420 has been performed. For example, the values of the gyroscope data for the secondary rotation axes are set to zero and the accelerometer data for the primary rotation axis is set to zero.

Consider an example where the x axis is the primary rotation axis. The gyroscope data for the primary rotation axis, $\omega_p$, corresponds to the x-axis gyroscope data, and the accelerometer data, $a_{s1}$, $a_{s2}$, represent accelerometer data for the secondary rotation axes, y, and z, respectively.

The suppressed accelerometer rotation angle, $\theta_a$, is calculated by:

$$\theta_a = \arctan\left(\frac{a_{s1}}{a_{s2}}\right). \quad (16)$$

The suppressed gyroscope rotation angle $\theta_g$, is calculated in an integrator 900 by integrating the gyroscope data for the primary rotation axis, $\omega_p$:

$$\theta_g = \theta_g + \omega_x * \Delta T. \quad (17)$$

The suppressed accelerometer rotation angle, $\theta_a$, is provided to a low pass filter 905 to generate a filtered accelerometer rotation angle, $\theta'_a$:

$$\theta'_a = (1-\alpha)*\theta_a + \alpha*\theta'_{a_{previous}}, \quad (18)$$

where $\alpha$ is the cut off threshold of the low pass filter 905.

The suppressed gyroscope rotation angle, $\theta_g$, is provided to a high pass filter 910 to generate a filtered gyroscope rotation angle, $\theta'_g$:

$$\theta'_g = (1-\alpha)*(\theta_g - \theta_{g_{previous}}) + (1-\alpha)*\theta'_{g_{previous}}, \quad (19)$$

The tilt angle, $\theta$, is derived by adding the accelerometer and gyroscope filtered rotation angles in a summation module 915:

$$\theta = \theta'_g + \theta'_a = \beta*\theta_g + (1-\beta)*\theta_a,$$

where $\beta$ is a weighting constant between 0 and 1. For example, a value of $\beta=0.5$ represents an equal weighting. The value of $\beta$ may be determined during a training interval of the system 100.

Figure 10:
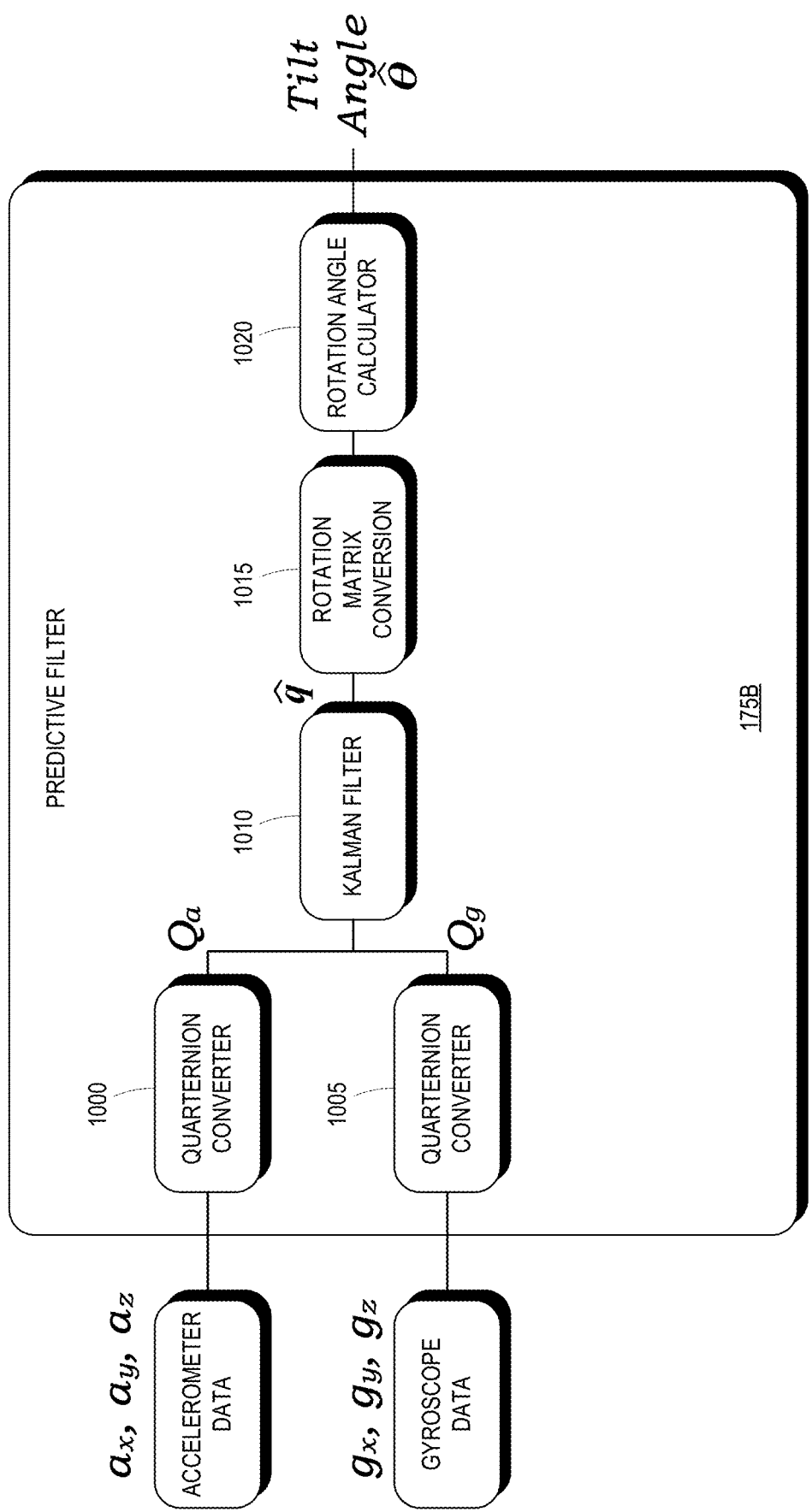
FIG. 10 is a simplified block diagram of a predictive filter, in accordance with some embodiments.

FIG. 10 is a simplified block diagram of the predictive filter 175B, in accordance with some embodiments. The predictive filter 175B fuses data from the accelerometer and the gyroscope using data that is not suppressed with respect to the primary rotation axis. The accelerometer data and the gyroscope data are provided to quaternion converter 1000, 1005, respectively. The quaternion converter 1000, 1005 convert the incoming 3D vectors to quaternions. In general, a quaternion is an expression of the form q=a+b*i+c*j+d*k, where a, b, c, d are real numbers, and i, j, k are symbols that can be interpreted as unit-vectors point along the three spatial axes. A quaternion includes a scalar part, a, and a vector part, b*i+c*j+d*k.

The quaternion converter 1000 calculates an accelerometer quaternion using:

$$G_a = \sqrt[2]{a_x * a_x + a_y * a_y + a_Z * a_Z}, \text{ and} \tag{20}$$

$$Q_a = \cos\left(\frac{G_a}{2}\right) + \sin\left(\frac{G_a}{2}\right) * a_x * i + \sin\left(\frac{G_a}{2}\right) * a_y * j + \sin\left(\frac{G_a}{2}\right) * a_Z * k. \tag{21}$$

The quaternion converter 1005 calculates a gyroscope quaternion using:

$$G_g = \sqrt[2]{g_x * g_x + g_y * g_y + g_Z * g_Z} \text{ and} \tag{22}$$

$$Q_g = \cos\left(\frac{G_g}{2}\right) + \sin\left(\frac{G_g}{2}\right) * g_x * i + \sin\left(\frac{G_g}{2}\right) * g_y * j + \sin\left(\frac{G_g}{2}\right) * g_Z * k. \tag{23}$$

The quaternions are received by a Kalman filter 1010. The Kalman filter has the form:

$$\hat{q}_k = F_k * q_{k-1} + B_k * (q_k - z_k), \tag{24}$$

where $F_k$ is the prediction matrix and $B_k$ is the control matrix. The output of the Kalman filter is also a quaternion of the form:

$$\hat{q} = a + b*i + c*j + d*k. \tag{25}$$

A rotation matric conversion module 1015 converts the quaternion output by the Kalman filter 1010 to a rotation matrix:

$$R = \begin{pmatrix} a^2 + b^2 - c^2 - d^2 & 2bc - 2ad & 2bd + 2ac \\ 2bc + 2ad & a^2 - b^2 + c^2 - d^2 & 2cd - 2ab \\ 2bd - 2ac & 2cd + 2ab & a^2 - b^2 - c^2 + d^2 \end{pmatrix}. \tag{26}$$

A rotation angle calculator 1020 calculates rotation angles $\hat{\theta}$ along each axis using:

$$\theta_x = \text{atan2}(2cd + 2ab, a^2 - b^2 - c^2 + d^2) \tag{27}$$

$$\theta_y = \text{atan2}\left(2ac - 2bd, \sqrt[2]{(2cd + 2ab)^2 + (a^2 - b^2 - c^2 + d^2)^2}\right)$$

$$\theta_z = \text{atan2}(2bc + 2ad, a^2 + b^2 - c^2 - d^2)$$

The ROM estimator 175 selects the rotation angle generated by the predictive filter 175B as the rotation angle as the output value. In some embodiments, the ROM estimator 175 averages the rotation angles generated by the complementary filter 175A and the predictive filter 175B to generate the ROM for the motion associated with the motion interval.

The classification of motions and the determining of the range of motion provides a wearable-based system that can aid therapeutic providers in joint motion measurements. The motion sensor 140 employs sensors built into off-the-shelf wearable devices and works robustly in different indoor environments. The motion sensing system 100 automatically identifies and evaluates motions, providing a convenient measurement system. The motion sensing system 100 is also useful in an educational environment for training therapeutic providers. The motion sensing system 100 accurately identifies different motions and provides reliable ROM measurements for both active and passive joint motions.

Figure 11:
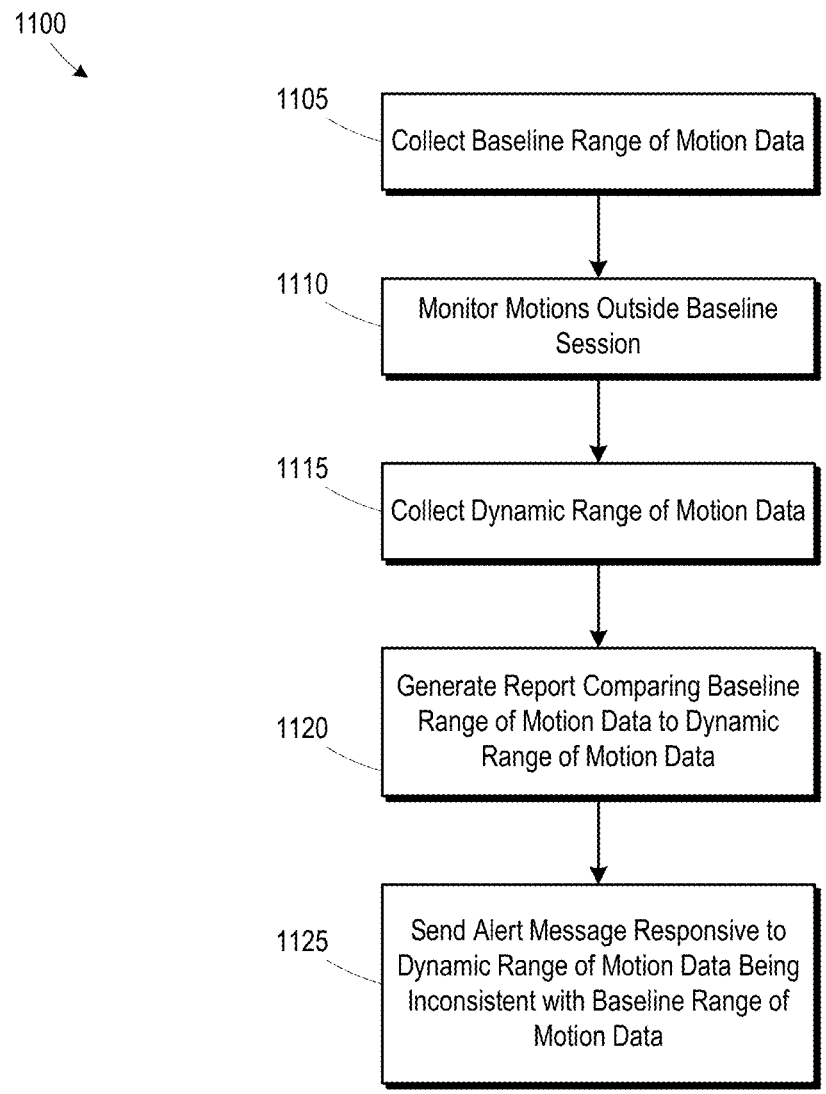
FIG. 11 is a flow diagram of an illustrative method for comparing baseline range of motion data to dynamic range of motion data, in accordance with some embodiments.

FIG. 11 is a flow diagram of an illustrative method 1100 for comparing baseline range of motion data to dynamic range of motion data, in accordance with some embodiments. For example, the baseline range of motion data may represent data collected during a controlled session, such as a medical examination, a physical or occupational therapy session, an exercise session, a training session, a coaching session, etc. The dynamic range of motion data may represent a continuous tracking mode that monitors the user's motions outside the controlled session.

In some embodiments, the motion sensing system 100 is employed to track characteristics of the user's motions over time. For example, the user's range of motion for a particular joint may be monitored. During a baseline session, a user may be instructed to perform various movements to provide information regarding joint health. In method block 1105, baseline range of motion data 190 (see FIG. 1) is collected, in accordance with some embodiments. In some embodiments, the baseline range of motion data 190 includes range of motion measurements for one or more joints and one or more motions. The baseline range of motion data 190 may include a list of motions and one or more entries including range of motion measurements for each motion collected during the baseline session. Techniques for classifying the motions using the motion classifier 170 and determining the range of motion for each motion using the ROM estimator 175 are described above. In some embodiments, the baseline range of motion data 190 is recorded by the motion supervisor application 162 responsive to an input received by the motion supervisor application 162 using the display 135 or in response to a voice command. A therapist may participate in the collection of the baseline range of motion data 190 and interface with the motion supervisor application 162. In some embodiments, the therapist provides identification credentials to the motion supervisor application 162 to enable the baseline session mode and the collection of the baseline range of motion data 190. In this manner, the collection of the baseline range of motion data 190 is controlled by an entity other than the user. In some embodiments, the user may indicate transitions between the controlled session and the continuous tracking modes by interfacing with the mobile device 155, such as with a control on the display 135 of the mobile device.

In method block 1110, the motion supervisor application 162 dynamically monitors user motions outside the baseline session. For example, during normal activity, the user may perform various activities that involve motions corresponding to motions that were stored in the baseline range of motion data 190. For example, the user may perform various shoulder extension or abduction movements during normal activity throughout the day. The dynamic motion data may represent an essentially continuous monitoring of the user.

In method block 1115, the motion supervisor application 162 collects dynamic range of motion data 195 (see FIG. 1) by receiving motion classification data from the motion classifier 170 and range of motion data for each motion from the ROM estimator 175. The motion supervisor application 162 generates a list of classified motions and the resulting range of motion measurements for the dynamic motions occurring outside the baseline session. In some embodiments, the motion supervisor application 162 only generates entries for the specific motions included in the baseline range of motion data 190. In some embodiments, the motion supervisor application 162 generates entries for a set of motions associated with a particular joint, including motions other than those in the baseline range of motion data 190. In general, the baseline range of motion data 190 represents motion data collected during a controlled session, while the dynamic range of motion data 195 represents data collected during the user's normal activities outside the controlled session.

In method block 1120, the motion supervisor application 162 generates a motion summary report 197 (see FIG. 1) comparing the baseline range of motion data 190 to the dynamic range of motion data 195. In some embodiments, the motion summary report 197 lists the tracked movements and provides both the baseline range of motion data 190 and the dynamic range of motion data 195 for those movements. The range of motion measurements for both the baseline range of motion data 190 and the dynamic range of motion data 195 may be averaged, plotted on a curve, etc.

In some embodiments, a report including the baseline range of motion data and the dynamic range of motion data for tracked movements is sent to an external party, such as a doctor, a therapist, a trainer, a coach, etc. The report facilitates a comparison between the baseline range of motion data collected for the controlled session and the dynamic range of motion data collected during a continuous tracking mode.

In some embodiments, the motion summary report 197 includes a difference metric indicating the degree to which the dynamic range of motion data 195 differs from the baseline range of motion data 190. In some situations, a user's range of motion during the baseline session may differ from the range of motion seen in dynamic motions occurring in normal activity. In one example, the baseline session may be a medical, therapy, training, or coaching session, and the user may be hesitant during the session, leading to reduced range of motion in the baseline session. In some cases, this hesitancy may be subconscious. In other situations, a user may intentionally restrict the range of motion to attempt to make an injury appear more severe.

In some embodiments, the difference metric may indicate that the dynamic range of motion data 195 indicates an increased range of motion relative to the baseline range of motion data 190. In some embodiments, the dynamic range of motion data 195 may be used to provide further instruction to the user to encourage the user to be less hesitant during therapy sessions. In some embodiments, the dynamic range of motion data 195 is used for fraud detection. If a user exaggerates an injury for purposes of obtaining some sort of compensation, data in the dynamic range of motion data 195 may demonstrate this exaggeration. For example, the dynamic range of motion data 195 may indicate that the user has more range of motion than demonstrated in the baseline range of motion data 190 during the controlled session. In some embodiments, the difference metric may indicate that the dynamic range of motion data 195 indicates a decreased range of motion relative to the baseline range of motion data 190. This situation may be indicative of a worsening of the user's condition and may warrant further intervention by a therapist.

In method block 1125, the motion supervisor application 162 sends an alert message responsive to the dynamic range of motion data 195 being inconsistent with the baseline range of motion data 190. An inconsistency between the data may be indicative of a need for further intervention by a therapist or the inconsistency may indicate fraud. In some embodiments, the motion supervisor application 162 sends the alert message through an independent channel not controlled by the user. For example, the motion supervisor application 162 may send the alert message via the remote computing resource 185 using a dedicated or encrypted channel. In some embodiments, the motion supervisor application sends the alert message via email or text message. For example, the alert message may be sent if the difference metric indicates that the dynamic range of motion data 195 differs from the baseline range of motion data 190 by a predetermined percentage.

Figure 12:
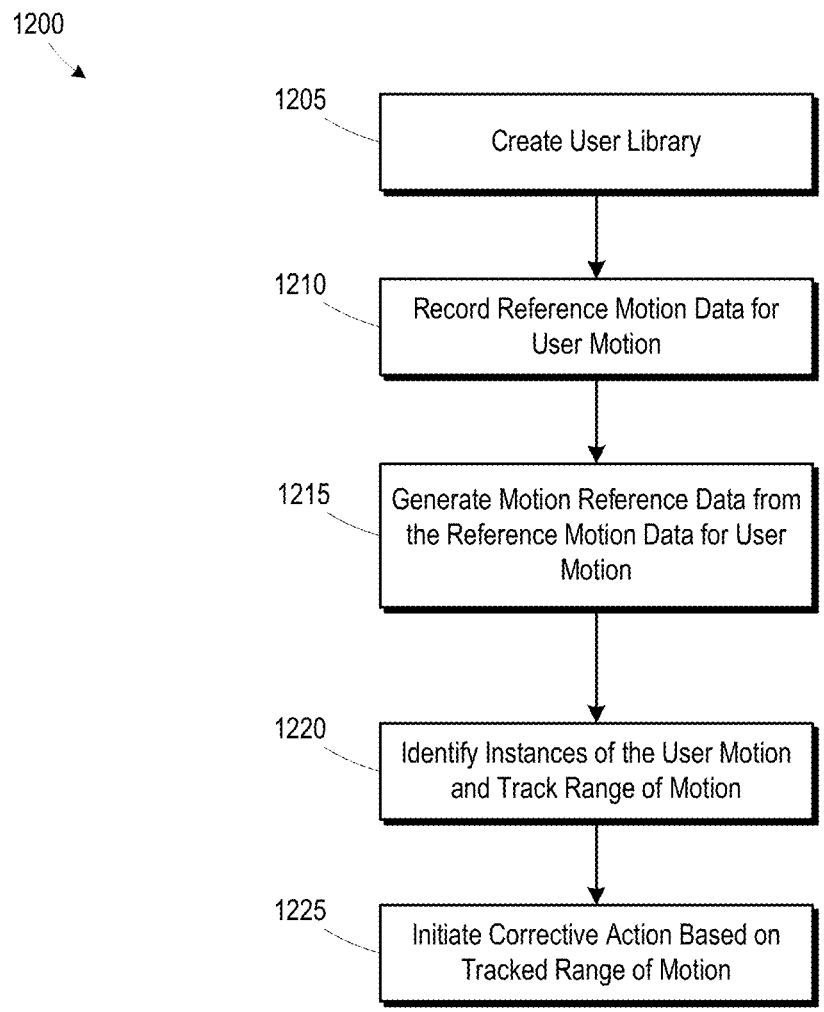
FIG. 12 is a flow diagram of an illustrative method for generating a user library including reference time series specific to the user, in accordance with some embodiments.

FIG. 12 is a flow diagram of an illustrative method 1200 for generating a user library 180B including reference time series specific to the user, in accordance with some embodiments. As described above, the global library 180A is preconfigured with reference motion time series for a specific set of movements. In method block 1205 a user library 180B is created. The user library 180B allows additional reference time series specific to the user to be stored. In some embodiments, the reference time series specific to the user are added to the user library 180B during a training session, such as a therapy session. A therapist or trainer may participate in the collection of the reference entries for the user library 180B and interface with the motion supervisor application 162. In some embodiments, the therapist or trainer provides identification credentials to the motion supervisor application 162 to enable the training session for adding to the user library 180B. In this manner, the collection of the reference entries for the user library 180B is controlled by an entity other than the user. In some embodiments, the user motions comprise athletic motions, such as exercise motions, weightlifting motions, golf swing motions, tennis swing motions, swimming stroke motions, etc. In some embodiments, the user motions comprise job-related motions, such as lifting motions.

In method block 1210, motion reference data is recorded for a user motion. The motion data includes accelerometer and gyroscope data. In some embodiments, the motion data includes magnetic sensor data. In some embodiments, the therapist observes the user performing the user motion and provides input to the motion supervisor application 162 to store a particular set of motion data responsive to the motion being performed correctly. In some embodiments, the user motion corresponds to an existing motion in the global library 180A. In some embodiments, the user motion is a new motion that does not have a corresponding entry in the global library 180A. The therapist specifies a classification for the captured motion (i.e., provides a name for the motion).

In method block 1215, the motion supervisor application 162 generates motion reference data for the user motion from the captured motion data. In some embodiments, the reference motion data for the user motion is processed by the feature extraction unit 170B to extract features from the motion data for the user motion. In some embodiments, a PCA technique is used to extract the features for the user motion, as described above. The motion supervisor application 162 stores the data generated by the feature extraction unit 170B as the reference time series with known classification as an entry in the user library 180B. In some embodiments, the therapist may capture reference data for multiple instances of the user motion. For example, the motion may be performed at different speeds.

In some embodiments, the motion supervisor application 162 performs the steps of FIG. 4 when generating the entries in the user library 180B. For example, the motion interval is detected (see method block 410), the primary axis of rotation is identified (see method block 415), and the secondary axes of rotation are suppressed (see method block 410) when the feature extraction is performed to generate the motion reference data for the user motions. The motion data with the suppressed secondary axes data is stored in the user library 180B.

In method block 1220, the motion supervisor application 162 identifies instances of the user motion and tracks range of motion. The motion supervisor application 162 may dynamically monitor user motions to identify when the user performs the user motion, such as during normal activities or during a subsequent therapy session. The motion classifier 170 identifies occurrences of the user motion as described above by matching an incoming motion with the entry in the user library 180B. In some embodiments, the motion classifier 170 applies a weighting factor to the entries in the user library 180B to give preference to entries in the user library 180B, since they are known to be motions performed by the specific user. The ROM estimator 175 is employed as described above to generate range of motion measurements for the user motion. In some embodiments, the motion supervisor application 162 generates a list of instances of the use motion and the resulting range of motion measurements for the user motions. In some embodiments, the motion summary report 197 (see FIG. 1) includes ROM data for the user motion.

In method block 1225, the motion supervisor application 162 initiates a corrective action based on the tracked range of motion. If an adverse trend is identified in the range or motion data, the motion supervisor application 162 sends an alert message. In some embodiments, the motion supervisor application 162 sends the alert message through an independent channel not controlled by the user. For example, the motion supervisor application 162 may send the alert message via the remote computing resource 185 using a dedicated or encrypted channel. In some embodiments, the motion supervisor application sends the alert message via email or text message.

In some instances, the user may be instructed to intentionally practice the user motion in an independent or monitored therapy session to allow the motion summary report 197 to be generated during the therapy session and to be viewed by the therapist. In some embodiments, the user provides an input to the motion supervisor application 162 on the display 135 or via voice command to initiate the collection of data for the motion summary report 197. After completion of the session, the user provides an additional input, and the motion summary report 197 is sent to the therapist. In some embodiments, the user may be performing the motion incorrectly. The motion supervisor application 162 may identify this situation if, after the user initiates the therapy session to practice the user motion, the motion classifier 170 identifies other motions in the global library 180A or the user library 180B that do not correspond to the user motion. Hence, if other motions are identified during the tracking of the range of motion in method block 1220, the corrective action in method block 1225 includes providing instruction to the user regarding the expected user motion. In some embodiments, a message may be provided on the display 135 that the user may be performing the motion incorrectly. During the creation of the motion data in the user library 180B, the therapist may record a video of the user performing the user motion. The video or a link to the video may be stored in the user library 180B with the associated user motion. The message on the display 135 may include a control that allows the user to view the video to receive instruction on the proper motion.

A method includes collecting reference motion data in a device from a motion sensor worn by a user for a movement having a predetermined classification. The motion sensor is attached to a limb having a joint. A user library entry is generated in the device based on the reference motion data and the predetermined classification. Additional motion data is collected in the device from the motion sensor. User motions in the additional motion data corresponding to the user library entry are classified in the device. Range of motion data associated with the user motions is generated in the device. A report is generated in the device including the user motions and the associated range of motion data.

A system includes a motion sensor to collect motion data for a limb having a joint. A device comprising a processor communicates with the motion sensor. The processor is to collect reference motion data for a movement having a predetermined classification when the motion sensor is worn by a particular user, generate a user library entry in the device based on the reference motion data and the predetermined classification, collect additional motion data from the motion sensor, classify user motions in the additional motion data in the device corresponding to the user library entry, generate range of motion data associated with the user motions, and generate a report in the device including the user motions and the associated range of motion data. In some embodiments, certain aspects of the techniques described herein may implemented by one or more processors of a processing system executing software. The software comprises one or more sets of executable instructions stored or otherwise tangibly embodied on a non-transitory computer readable storage medium. The software can include the instructions and certain data that, when executed by the one or more processors, manipulate the one or more processors to perform one or more aspects of the techniques described above. The non-transitory computer readable storage medium can include, for example, a magnetic or optical disk storage device, solid state storage devices such as flash memory, a cache, random access memory (RAM), or other non-volatile memory devices, and the like. The executable instructions stored on the non-transitory computer readable storage medium may be in source code, assembly language code, object code, or other instruction format that is interpreted or otherwise executable by one or more processors.

A non-transitory computer readable storage medium may include any storage medium, or combination of storage media, accessible by a computer system during use to provide instructions and/or data to the computer system. Such storage media can include, but is not limited to, optical media (e.g., compact disc (CD), digital versatile disc (DVD), Blu-Ray disc), magnetic media (e.g., floppy disc, magnetic tape, or magnetic hard drive), volatile memory (e.g., random access memory (RAM) or cache), non-volatile memory (e.g., read-only memory (ROM) or Flash memory), or microelectromechanical systems (MEMS)-based storage media. The computer readable storage medium may be embedded in the computing system (e.g., system RAM or ROM), fixedly attached to the computing system (e.g., a magnetic hard drive), removably attached to the computing system (e.g., an optical disc or Universal Serial Bus (USB)-based Flash memory), or coupled to the computer system via a wired or wireless network (e.g., network accessible storage (NAS)).

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific embodiments. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims. Moreover, the particular embodiments disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular embodiments disclosed above may be altered or modified and all such variations are considered within the scope of the disclosed subject matter. Accordingly, the protection sought herein is as set forth in the claims below.

What is claimed is:

1. A method, comprising:
   collecting reference motion data in a device from a motion sensor configured to be worn by a user for a movement having a predetermined classification, wherein the motion sensor is configured to be attached to a limb having a joint, the predetermined classification identifies a type of movement of the joint, and the reference motion data comprises accelerometer data and gyroscope data;
   determining a primary rotation axis from a plurality of motion axes based on the reference motion data;
   suppressing a portion of the reference motion data based on the determined primary rotation axis by suppressing the gyroscope data for axes other than the primary rotation axis and suppressing the accelerometer data for the primary rotation axis to generate suppressed motion data;
   generating a user library entry in the device based on the suppressed reference motion data and the predetermined classification;
   collecting additional motion data in the device from the motion sensor;
   classifying user motions in the additional motion data corresponding to the user library entry in the device;
   generating range of motion data in the device associated with the user motions; and
   generating a report in the device including the user motions and the associated range of motion data.

2. The method of claim 1, wherein determining the primary rotation axis comprises:
   identifying a selected accelerometer axis having a minimum standard deviation;
   identifying a selected gyroscope axis having a maximum rotation angle; and
   selecting one of the axes as the primary axis rotation responsive to the selected accelerometer axis matching the selected gyroscope axis.

3. The method of claim 1, wherein determining the primary rotation axis comprises:
   identifying a selected accelerometer axis having a minimum standard deviation;
   identifying a first selected gyroscope axis having a maximum rotation angle;
   identifying a second selected gyroscope axis having an earliest rotation movement; and
   selecting one of the axes as the primary axis rotation based on a majority voting across the selected accelerometer axis, the first selected gyroscope axis, and the second selected gyroscope axis.

4. The method of claim 3, further comprising eliminating a selected axis sensing gravity in an initial portion of the reference motion data as a candidate for the primary rotation axis.

5. The method of claim 1, further comprising:
   generating an incoming motion time series by combining the suppressed accelerometer data and the suppressed gyroscope data; and
   generating the user library entry based on the incoming motion time series by performing a principal components analysis feature extraction on the suppressed accelerometer data and the suppressed gyroscope data.

6. A system, comprising:
   a motion sensor to collect motion data for a limb having a joint; and
   a device comprising a processor communicating with the motion sensor, wherein the processor is to:
      collect reference motion data for a movement having a predetermined classification when the motion sensor is worn by a particular user, wherein the predetermined classification identifies a type of movement of the joint and the reference motion data comprises accelerometer data and gyroscope data;
      determine a primary rotation axis from a plurality of axes based on the reference motion data;
      suppress a portion of the reference motion data based on the determined primary rotation axis by suppressing the gyroscope data for axes other than the primary rotation axis and suppressing the accelerometer data for the primary rotation axis to generate suppressed motion data;
      generate a user library entry in the device based on the suppressed reference motion data and the predetermined classification;
      collect additional motion data from the motion sensor;
      classify user motions in the additional motion data in the device corresponding to the user library entry;
      generate range of motion data associated with the user motions; and
      generate a report in the device including the user motions and the associated range of motion data.

7. The system of claim 6, wherein the processor is to determine the primary rotation axis by:
   identifying a selected accelerometer axis having a minimum standard deviation;
   identifying a selected gyroscope axis having a maximum rotation angle; and
   selecting one of the axes as the primary axis rotation responsive to the selected accelerometer axis matching the selected gyroscope axis.

8. The system of claim 6, wherein the processor is to determine the primary rotation axis by:

identifying a selected accelerometer axis having a minimum standard deviation;
identifying a first selected gyroscope axis having a maximum rotation angle;
identifying a second selected gyroscope axis having an earliest rotation movement; and
selecting one of the axes as the primary axis rotation based on a majority voting across the selected accelerometer axis, the first selected gyroscope axis, and the second selected gyroscope axis.

9. The method of claim 8, wherein the processor is to eliminate a selected axis sensing gravity in an initial portion of the motion data as a candidate for the primary rotation axis.

10. The system of claim 6, wherein the processor is to:
generate an incoming motion time series by combining the suppressed accelerometer data and the suppressed gyroscope data; and
generate the user library entry based on the incoming motion time series by performing a principal components analysis feature extraction on the suppressed accelerometer data and the suppressed gyroscope data.

* * * * *